United States Patent [19]
deAlwis

[11] Patent Number: 5,817,525
[45] Date of Patent: Oct. 6, 1998

[54] STABLE PROTEIN SOLUTIONS FOR DIAGNOSTICS AND METHOD OF MAKING AND USING THE SAME

[75] Inventor: Uditha deAlwis, Walpole, Mass.

[73] Assignee: Chiron Diagnostics Corporation, Walpole, Mass.

[21] Appl. No.: 445,157

[22] Filed: May 19, 1995

[51] Int. Cl.⁶ ...................... G01N 33/543; G01N 33/551; G01N 33/553; G01N 33/552
[52] U.S. Cl. .................... 436/523; 436/518; 436/524; 436/525; 436/526; 436/527; 436/528; 436/529; 436/530; 436/531; 435/4; 435/7.1; 435/7.2
[58] Field of Search ............................ 436/518, 523–531; 435/4, 7.1, 7.2

[56] References Cited

U.S. PATENT DOCUMENTS 4,554,088  11/1985  Whitehead .

FOREIGN PATENT DOCUMENTS

| | | |
|---|---|---|
| 0 303 980 A3 | 2/1989 | European Pat. Off. . |
| 0 341 439 A1 | 11/1989 | European Pat. Off. . |
| 0 528 499 A1 | 2/1993 | European Pat. Off. . |
| 2 052 059 | 1/1981 | United Kingdom . |

OTHER PUBLICATIONS

Sigma Catalogue; Biochemicals, Organic Compounds for Research and Diagnostic Reagents; 1991 XPOO2013871; Product nrs. A 6285 and A 0161.

Liu, Robert W. et al., Moisture–Induced Aggregation of Lyophilized Proteins in the Solid State, Biotechnology & Bioengineering, 37, pp. 77–184 (1991).

*Primary Examiner*—Lila Feisee
*Assistant Examiner*—Sheela J. Huff
*Attorney, Agent, or Firm*—Arthur S. Morgenstern; Robert P. Blackburn

[57] ABSTRACT

The present invention features stable bulking agents and blocking agents for solid phase materials containing proteins. The proteins have thiol groups which are blocked or chemically inert, preventing the formation of aggregates. Chemical solutions wherein thiol groups, if present, are blocked or chemically inert, are particularly useful in analytical applications and in diagnostic reagents utilizing solid phase materials or particles.

15 Claims, 4 Drawing Sheets

STABLE PROTEIN SOLUTIONS FOR DIAGNOSTICS AND METHOD OF MAKING AND USING THE SAME

BACKGROUND OF THE INVENTION

The invention relates to solutions containing dissolved proteins which are used or stored in plastic containment vessels and methods of making and using such solutions. Such protein solutions are commonly used in analytical or diagnostic applications as bulking agents. That is, the proteins impart on the aqueous solution an environment of viscosity and electrogenic character which is consistent with a biological environment. The invention also relates to blocking agents coupled to solid phase materials or particles.

Diagnostic products are increasingly using solid phase materials, including particles having binding partners attached thereto in order to effect capture of an analyte. The solid phase materials or particles are dispersed in the aqueous medium to form a reagent suspension having kinetics which mimic in solution reactions. Typically, the particles are isolated after the analyte is captured.

A particularly useful particle is a paramagnetic particle. Paramagnetic particles having an attached binding partner are used in diagnostic kits for the detection of various analytes. In these kits, the binding partner is specific to a reactant or analyte sought to be detected and quantitated. In the presence of analyte in a test sample, a binding partner/reactant complex is formed. This complex can be detected with signal developing reagents. Signal developing reagents may comprise further binding partners to the analyte which carry a label for detection.

Paramagnetic particles are typically of micron size and are normally invisible to the naked eye. The small size of the particle allows such particle to be readily dispersed in an aqueous medium and readily isolated with a magnetic field. Paramagnetic particles are made or are processed to provide a reactive or silane coat on their surface. The coating provides an attachment site for further reactive species or binding partners on the surface of the particle. The particles are first chemically activated to couple the reactive or silane coating, by known chemistries, to the surface. The silane coating offers a reactive moiety to couple binding partners to the particle surface.

The chemically activated particle is then placed in contact with a binding partner which needs to be attached to the particle. For example, an antibody that is specific to an analyte of interest. The reaction is performed typically in excess of the binding partner to ensure a complete reaction. After coupling the protein to the particle, the excess protein is removed by reacting the particle with bovine serum albumin (BSA) at 50° C. Reacting the particle with BSA at 50° is commonly referred to as a heat stress reaction or blocking agent reaction. The finished particle is then suspended in a buffer containing BSA and other protein, i.e. a bulking agent. In commercial use, products or reagent suspensions of this type are often packaged in plastic bottles and shipped to end users.

The bulking agent solutions of the prior art are not particularly stable. Even with refrigeration, such solutions show evidence of degradation. In solutions suspending particles, the particles, over time, form clumps which are visible to the naked eye, even though the products are stored at 4° C. This problem is particularly severe where the pH of the solution is above 7.5. The problem also manifests itself where the bulking agents are maintained in containment vessels comprising normal laboratory plastics, such as polyethylene, polyethyletetrathalate, polystyrene, polycarbonate, and polypropylene. Movement or agitation of the solution also increases the rate of aggregate or fibril formation.

NOMENCLATURE

The following definitions are provided to facilitate a clear understanding of the present invention. It is noted that the use of terms in a singular tense should not be construed as to limit the applicability of the terms to use in the plural tense, i.e. binding partner or binding partners.

The term "binding partner/reactant" refers to any pair of molecules which exhibits affinity, complexation or binding capacity, typically specific binding or interacting (complex-forming) or annealing pairs, such as antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, repressor/inducer, and the like.

The term "binding partner" refers to that member of a binding partner/reactant pair which is coupled to a solid phase.

The term "blocking agent" refers to a material which, on being coated to a solid phase, reduces non-specific binding while allowing less than maximal binding partner loading to the solid phase.

The term "reactant" refers to that member of a binding partner/reactant complex, the existence and/or concentration of which is to be determined, or the recovery of which is desired, and which is to be captured by the binding partner from a medium in which it is dispersed. An analyte in a test medium is an exemplary reactant, as is a specifically-binding industrial reagent to be recovered.

The term "test assay" generally refers to any procedure in which a member of a binding partner/reactant in a test sample is to be detected and/or quantitated in a medium by various assay formats. For example, "test assay" may be used to describe a diagnostic procedure, analytical procedure, microanalytical procedure, forensic analysis, pharmacokinetic study, cell sorting procedure, affinity chromatogram, industrial or laboratory recovery or analysis of one or more species such as toxins, catalysts, or starting materials or products, and the like. The term may be used to describe a procedure in which a plurality of reagents, each including a different binding partner, is employed to capture a plurality of corresponding reactants. A typical test assay is an immunoassay.

The term "complex" refers to the specific binding or interaction or association of two or more species, for example, a binding partner and reactant.

The term "capturing" refers to the analysis, recovery, detection, or other qualitative or quantitative determination of a reactant in a medium, for example via complexation in a test assay. As an example, in a sandwich immunoassay, a surface-coupled binding partner will form a complex with a reactant, before or after the reactant forms a complex with another (generally labeled) binding partner or reactant. In a competitive assay, labeled and unlabeled reactants typically compete for complexation with a surface-coupled binding partner.

The term "inert" refers to a chemical or biological state in which a material does not interact with the binding partner of the test assay in which it is employed in the way in which the binding partner and reactant interact. The term may also refer to a chemical or biological state in which the material does not chemically interact with other reactive moities in a test reaction or reagent suspension.

The term "solid phase" refers to any material which is insoluble in a medium containing a reactant to be captured in a particular test assay. In a broad sense, the term describes any entity which can be substantially dispersed within a medium and removed or separated from the medium by immobilization, filtering, partitioning, centrifugation or into which the medium can be dispensed, or the like. A blocking agent may be attached to the solid phase to reduce non-specific binding.

The term "reagent suspension" refers generally to a processed material modified to participate in a complexing reaction such as a test assay, more specifically to a solid phase material to which a binding partner is coupled and suspended in a bulking agent solution.

The term "non-specific binding" (NSB) refers to a non-desired interaction between a reagent and any other species present in a test assay other than binding partner/reactant complexation.

The term "label" refers to an atom or a molecular moiety capable of generating a signal for detection of the binding reaction. It includes, without limitation, radioactive isotopes, enzymes, luminescent agents, precipitating agents, and dyes.

The term "sample" refers to any medium containing a reactant or analyte to be captured and detected and quantitated in a test assay.

The term "analyte" refers to any hormone, pharmacologic agent, vitamin or cofactor, hematological substances, virus antigens, nucleic acids, nucleotides, allergens, or other markers sought to be detected and quantitated.

The term "substitutions" refers to the substitution of nitrogen for one or more carbons.

The term "derivative thereof" refers to an addition of a nitrogen containing functional group.

SUMMARY OF THE INVENTION

The present invention features articles of manufacture and methods for making a reagent suspension of solid phase material or particles and bulking agents. The suspension retards the formation of protein aggregate or fibril formation. One embodiment of the present invention features a suspension of solid phase materials or particles suspended or disposed in an aqueous medium, comprising a thiol blocked chemical, preferably a thiol blocked protein. The thiol blocked protein has the formula:

P—X wherein P is a protein having one or more thiol groups. As used above, X is a blocking group covalently bonded to the S of the thiol group. Blocking groups for reaction with thiol groups are well known in the art. Representative blocking groups comprise of $C_1$–$C_{12}$ alkyl, $C_3$–$C_{12}$ cycloalkyl, $C_1$–$C_{12}$ haloalkyl, $C_1$–$C_{12}$ hydroxyalkyl. $C_2$–$C_{12}$ alkenyl, $C_2$–$C_{12}$ haloalkenyl, $C_2$–$C_{12}$ hydroxyalkeyl, $C_2$–$C_{12}$ alkynyl, $C_2$–$C_{12}$ haloalkynyl, $C_2$–$C_{12}$ hydroxyalkynyl $C_6H_5$, $C_1$–$C_{12}$ alkoxy, $C_1$–$C_{12}$ haloalkoxy, $C_1$–$C_{12}$ hydroxyalkoxy, $C_1$–$C_{12}$ alkylthio, $C_1$–$C_{12}$ alkylsulfinyl, $C_1$–$C_{12}$ alkylsulfonyl, and amine, amide, imide, substitutions and derivatives thereof.

The use of a thiol blocked protein in a reagent suspension retards the formation of fibrils or protein aggregates where the suspension of particles is stored in plastic bottles and which may also be subjected to movement.

Preferably, the protein, P, is albumin. The albumin may be derived from any source, any of which are commercially available. Common forms of albumin comprise human, bovine, porcine, cat, chicken, dog, donkey, egg, goat, guinea pig, hamster, horse, rat, rabbit, pigeon, sheep, rhesus monkey, turkey, as well as other sources.

Alternate chemical compositions may also be utilized as bulking agents and blocking agents, according to the present invention, provided that thiol groups, if present, are blocked or chemically inert.

Preferably, the particle is a paramagnetic particle.

A preferred X is a thiol alkyl group represented by the formula set forth below:

—S—R wherein R is $C_1$–$C_6$ alkyl, $C_3$–$C_6$ cycloalkyl, $C_1$–$C_6$ haloalkyl, $C_1$–$C_6$ hydroxyalkyl, $C_2$–$C_6$ alkenyl, $C_2$–$C_6$ haloalkenyl, $C_2$–$C_6$ hydroxyalkenyl, $C_2$–$C_6$ alkynyl, $2_3$–$C_6$ haloalkynyl, $C_2$–$C_6$ hydroxyakynyl, $C_6H_5$, $C_1$–$C_4$ alkoxy, $C_1$–$C_4$ haloalkoxy, $C_1$–$C_4$ hydroxyalkoxy, $C_1$–$C_4$ alkylthio, $C_1$–$C_4$ alkylsulfinyl, $C_1$–$C_4$ alkylsulfonyl, and amine, amide, imide, derivatives and substitutions thereof.

Preferably, the blocking group X may comprise a group set forth below:

$$-CH_2-\overset{\overset{\displaystyle O}{\|}}{C}-Z$$

As used above, Z is hydroxyl, $C_1$–$C_6$ alkyl, $C_3$–$C_6$ cycloalkyl, $C_1$–$C_6$ haloalkyl, $C_1$–$C_6$ hydroxyalkyl, $C_2$–$C_6$ alkenyl, $C_2$–$C_6$ haloalkenyl, $C_2$–$C_6$ hydroxyalkenyl, $C_2$–$C_6$ alkynyl, $C_2$–$C_6$ haloalkynyl, $C_2$–$C_6$ hydroxyalkynyl, $C_6H_5$, $C_1$–$C_4$ alkoxy, $C_1$–$C_4$ haloalkoxy, $C_1$–$C_4$ hydroxyalkoxy, $C_1$–$C_4$ alkylthio, $C_1$–$C_4$ alkylsulfinyl, $C_1$–$C_4$ alkylsulfonyl, and amine, amide, and imide substitutions and derivatives thereof, or Z is represented by the formula:

$$-\overset{\overset{\displaystyle U}{|}}{N}-W$$

wherein U and W independently are hydrogen, $C_1$–$C_6$ alkyl, $C_3$–$C_6$ cycloalkyl, C–$C_6$ haloalkyl, $C_1$–$C_6$ hydroxyalkyl, $C_2$–$C_6$ alkenyl, $C_2$–$C_6$ haloalkenyl, $C_2$–$C_6$ hydroxyalkenyl, $C_2$–$C_6$ alkynyl, $C_2$–$C_6$ haloalkynyl, $C_2$–$C_6$ hydroxyalkynyl, $C_6H_5$, $C_1$–$C_4$ alkoxy, $C_1$–$C_4$ haloalkoxy, $C_1$–$C_4$ hydroxyalkoxy, $C_1$–$C_4$ alkylthio, $C_1$–$C_4$ alkylsulfinyl, $C_1$–$C_4$ alkylsulfonyl, and amine, amide, and imide substitutions and derivatives thereof. Preferably, Z is $NH_2$.

A preferred X is represented by the formula below:

$$-(CH_2)_n-\overset{\overset{\displaystyle NH_2}{|}}{CH}-\overset{\overset{\displaystyle O}{\|}}{C}-OH$$

wherein n is an integer from 1–3. Preferably, n is 1.

Embodiments of the present invention further feature a method of making a reagent suspension. The method comprises the steps of combining water, a thiol blocked chemical compound, preferably a protein, and one or more particles having a binding partner attached thereto, to form an aqueous medium. The thiol blocked protein is placed in solution. The one or more suspended magnetic particles are suspended in the aqueous medium. The thiol blocked protein has the formula:

P—X wherein P is a protein having a thiol group and X is a blocking group covalently bonded to the thiol group. Blocking groups are known in the art and include $C_1$–$C_6$ alkyl, $C_3$–$C_6$ cycloalkyl, $C_1$–$C_6$ haloalkyl, $C_1$–$C_6$ hydroxyalkyl, $C_2$–$C_6$ alkenyl, $C_2$–$C_6$ haloalkenyl, $C_2$–$C_6$ hydroxyalkenyl, $C_2C_6$ alkynyl, $C_2$–$C_6$ haloalkynyl, $C_2$–$C_6$ hydroxyalkynyl, $C_6H_5$, $C_1$–$C_4$ alkoxy, $C_1$–$C_4$ haloalkoxy, $C_1$–$C_4$ hydroxyalkoxy, $C_1$–$C_4$ alkylthio, $C_1$–$C_4$ alkylsulfinyl, $C_1$–$C_4$ alkylsulfonyl, and amine, amide, and imide substitutions and derivatives thereof.

Preferably, the method further comprises the addition of appropriate buffers, inorganic or organic salts, and surfactants, i.e. triton, to the reagent suspension.

One embodiment of this invention is a method to detect the presence or absence of an analyte in a test sample. The analyte may be a chemical in a physiological fluid or other fluid or product for which analysis is to be made. The method comprises the steps of combining the sample to be tested, which may or may not contain the chemical or analyte or reactant, with the reagent suspension of this invention. The suspension comprises particles coated with a binding partner capable of reacting with the analyte, a thiol blocked bulking agent, and water. Ordinary reaction conditions are imposed on the suspension to form a reaction product or complex in the presence of the analyte, if present, and the suspension is monitored or detected by means of a label to determine the presence of the reaction product as an indication of the presence of the analyte. In some cases, the diagnostic or other analytical test for the analyte can be quantitative as well as qualitative in accordance with known practice.

It is, therefore, an object of the invention to provide a diagnostic reagent of a solid phase material or particle suspended in a chemical solution, preferably a protein solution, wherein thiol groups, if present, are blocked or chemically inert such that aggregates or fibril formation is retarded.

Another object of the invention is to provide diagnostic reagent of a solid phase material having coupled thereto a binding partner and a blocking agent which is devoid of chemically reactive thiol groups.

Another object of the invention is to provide a bulking agent for a diagnostic reagent, the bulking agent being a chemical solution wherein thiol groups, if present in the solution, are blocked or chemically inert.

A further objection of the invention is to provide a solid phase material having coupled thereto a binding partner and a blocking agent including a chemical compound wherein thiol groups, if present in the compound, are blocked or chemically inert.

Thus, the present invention features ways of stabilizing protein containing solutions used in in vitro applications, such as diagnostics. Embodiments of the present invention have particular application with respect to reagent suspensions. The reagent suspensions made in accordance with the present invention are stable and visible aggregates or fibril formation were retarded.

The features and advantages of the present invention will be apparent from the following description which, by way of illustration, shows preferred embodiments of the present invention and the principles thereof and what is now considered to be the best mode to apply these principles.

BRIEF DESCRIPTION OF THE DRAWINGS

The above and other features, objects and advantages of the present invention will be better understood from the following specification when read in conjunction with the accompanying drawings in which.

FIG. I is a series of color photographs showing various stages of fibril formation in a reagent suspension of the prior art.

DETAILED DESCRIPTION OF THE INVENTION

Figure 1A:
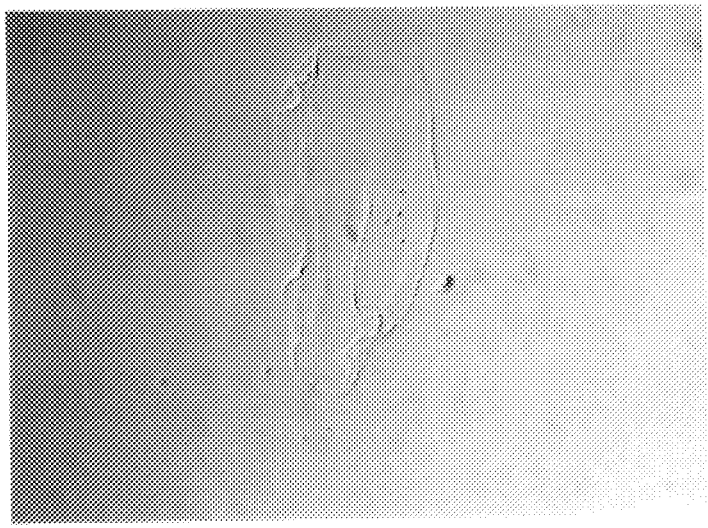

The present invention will be described in detail as an article of manufacture, a reagent suspension of particles or solid phase materials, and a method of making the same, with the understanding that the present disclosure is to be considered an exemplification of the principles of the invention and is not intended to limit the invention to the embodiment described. The present invention has application in analytical laboratory and diagnostic processes involving any reagent suspensions which exhibit a tendency to clump or aggregate. The reagent suspension of the present invention comprise a suspension of particles and a thiol blocked protein or chemical solution. A blocking agent comprising a thiol blocked chemical, preferably a protein is also provided.

The method and articles of manufacture of the present application have particular application with the use of paramagnetic particles as the solid phase material. Paramagnetic particles are described in U.S. Pat. No. 4,554,088, which reference is incorporated herein and are commercially available from Advanced Magnetics, Cambridge, MA. Diagnostic reagents employing such magnetic particles are commercially available from Ciba Corning Diagnostics Corp.

The described paramagnetic particles have a settling times in aqueous solutions of about 1.5 hours. The particles are about 0.1 to 101 in diameter and are responsive to low magnetic fields of 100–1000 oersteds. This particle size normally invisible to the naked eye.

Typically, these particles have an amino silane coating to act as attachment points for further reactive species or binding partners. Silane coating procedures are described in U.S. Pat. No. 3,652,761 and 4,554,088 and which references are incorporated herein. The particles are chemically activated with a reagent which couples to the amino silane and offers a reactive moiety to couple or attach binding partners to the particle surface. The reactive particles prepared are placed in contact with a binding partner which needs to be coupled to the particle. The reaction is typically performed in an excess of the binding partner to drive the reaction to completeness. The excess protein is removed by reacting the reagent with bovine serum albumin (BSA) at 50° C. Preferably, according to the present invention, a thiol blocked BSA is utilized as a blocking agent. This reaction is referred to as a heat stress reaction or blocking reaction. The coated particle is next placed in an aqueous buffer containing BSA and other proteins to form a reagent suspension. The BSA or other proteins, according to the present invention, are preferably thiol blocked and act as bulking proteins. These bulking proteins are biologically compatible but not reactive with the desired binding partner which is coupled to the particle surface and with the particle itself. The particles are packaged in plastic bottles, labeled and put in storage prior to shipping to customers.

Although stored for periods at 4° C., the prior art suspensions held in the packaged bottles develop, over time, clumps or aggregates or fibrils which are visible to the naked eye. Indeed, a polystyrene bottle filled with conventional protein solutions and subjected to a rocking motion for greater than one hour forms what appears to be fibrils or aggregates in the solution. It has been observed that a sheet of material forms and then folds over (becomes more dense) to appear as a series of strings or fibrils. The process of developing protein fibrils or aggregates is accelerated at pH 8.5 as compared to pH 7.5.

Figure 1B:
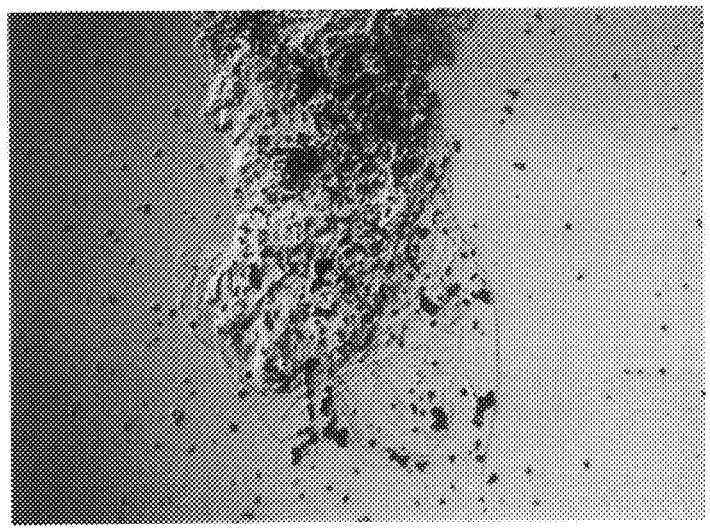
Figure 1C:
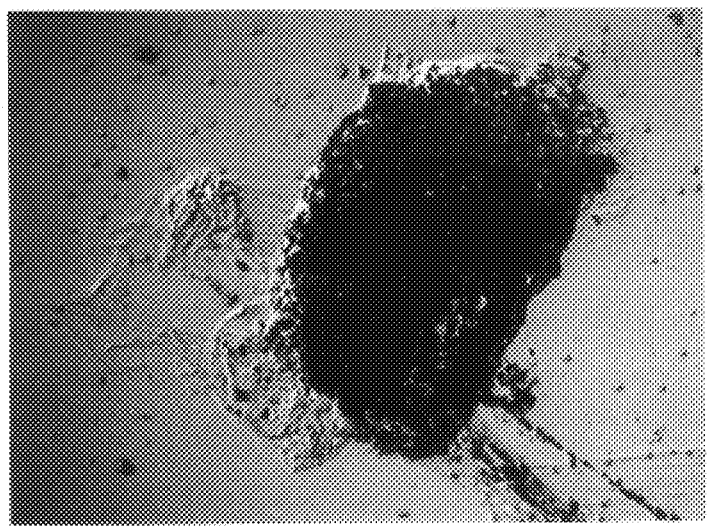

FIG. 1 shows a series of color photographs showing fibrils or aggregates in a reagent suspension of the prior art.

Using anti-BSA antibodies labeled with fluorescent labels, together with other antibodies which react with other protein constituents present in the buffer, labeled with non-interfering fluorescent labels, it was possible to identify the type of protein associated with the aggregate. These investigations suggest that the aggregates contain BSA. The fluorescent label aggregates appear to develop from a film which entangles particles. These films grow into clumps or aggregates which can be observed with the naked eye.

The particles, themselves, do not appear to contribute to the film making process. The films were formed on a template or surface, such as a water-air interface or a water-plastic interface. The formation of the film suggested a cross-linking reaction which caused stabilization of the monomer. The agglomeration reaction favored a high pH, elevated temperatures, the presence of plastic surfaces and fluid movement.

According to this invention, the bulking chemical agents, preferably proteins are treated to block thiol constituents thereof and thus form stable suspensions of this invention.

The thiol blocked protein has the formula:

wherein P is a protein having one or more thiol groups. As used above, X is a blocking group covalently bonded to the S of the thiol group. Blocking groups for reaction with thiol groups are well known in the art. Representative blocking groups comprise of $C_1$–$C_{12}$ alkyl, $C_3$–$C_{12}$ cycloalkyl, $C_1$–$C_{12}$ haloalkyl, $C_1$–$C_{12}$ hydroxyalkyl. $C_2$–$C_{12}$ alkenyl, $C_2$–$C_{12}$ haloalkenyl, $C_2$–$C_{12}$ hydroxyalkeyl, $C_2$–$C_{12}$ alkynyl, $C_2$–$C_{12}$ haloalkynyl, $C_2$–$C_{12}$ hydroxyalkynyl $C_6H_5$, $C_1$–$C_{12}$ alkoxy, $C_1$–$C_{12}$ haloalkoxy, $C_1$–$C_{12}$ hydroxyalkoxy, $C_1$–$C_{12}$ alkylthio, $C_1$–$C_{12}$ alkylsulfinyl, $C_1$–$C_{12}$ alkylsulfonyl, and amine, amide, imide, substitutions and derivatives thereof.

A preferred X is a thiol alkyl group represented by the formula set forth below:

wherein R is $C_1$–$C_6$ alkyl, $C_3$–$C_6$ cycloalkyl, $C_1$–$C_6$ haloalkyl, $C_1$–$C_6$ hydroxyalkyl, $C_2$–$C_6$ alkenyl, $C_2$–$C_6$ haloalkenyl, $C_2$–$C_6$ hydroxyalkenyl, $C_2$–$C_6$ alkynyl, $2_3$–$C_6$ haloalkynyl, $C_2$–$C_6$ hydroxyakynyl, $C_6H_5$, $C_1$–$C_4$ alkoxy, $C_1$–$C_4$ haloalkoxy, $C_1$–$C_4$ hydroxyalkoxy, $C_1$–$C_4$ alkylthio, $C_1$–$C_4$ alkylsulfnyl, $C_1$–$C_4$ alkylsulfonyl, and amine, amide, imide, derivatives and substitutions thereof.

Preferably, the blocking group X may comprise a group set forth below:

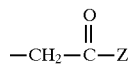

As used above, Z is hydroxyl, $C_1$–$C_6$ alkyl, $C_3$–$C_6$ cycloalkyl, $C_1$–$C_6$ haloalkyl, $C_1$–$C_6$hydroxyalkyl, $C_2$–$C_6$ alkenyl, $C_2$–$C_6$ haloalkenyl, $C_2$–$C_6$ hydroxyalkenyl, $C_2$–$C_6$ alkynyl, $C_2$–$C_6$ haloalkynyl, $C_2$–$C_6$ hydroxyalkynyl, $C_6H_5$, $C_1$–$C_4$ alkoxy, $C_1$–$C_4$ haloalkoxy, $C_1$–$C_4$hydroxyalkoxy, $C_1$–$C_4$ alkylthio, $C_1$–$C_4$ alkylsulfinyl, $C_1$–$C_4$ alkylsulfonyl, and amine, amide, and imide substitutions and derivatives thereof, or Z is represented by the formula:

wherein U and W independently are hydrogen, $C_1$–$C_6$ alkyl, $C_3$–$C_6$ cycloalkyl, $C_1$–$C_6$ haloalkyl, $C_1$–$C_6$ hydroxyalkyl, $C_2$–$C_6$ alkenyl, $C_2$–$C_6$ haloalkenyl, $C_2$–$C_6$ hydroxyalkenyl, $C_2$–$C_6$ alkynyl, $C_2$–$C_6$ haloalkynyl, $C_2$–$C_6$ hydroxyalkynyl, $C_6H_5$, $C_1$–$C_4$ alkoxy, $C_1$–$C_4$ haloalkoxy, $C_1$–$C_4$ hydroxyalkoxy, $C_1$–$C_4$ alkylthio, $C_1$–$C_4$ alkylsulfinyl, $C_1$–$C_4$ alkylsulfonyl, and amine, amide, and imide substitutions and derivatives thereof. Preferably, Z is $NH_2$.

A preferred X is represented by the formula below:

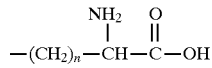

wherein n is an integer from 1–3. Preferably, n is 1.

Preferably, the suspensions are aqueous and are buffered to a pH of from 6.0 to 9.0 and preferably 7.5 to 8.5 and, more preferably, at 7.5. It is noted that the pH of the suspension is dependent, to some extent, on the binding partners, with some binding partners requiring a lower pH for the bulking agents. Conventional buffers comprise phosphate, borate, Goods buffers, PIPES, HEPES, MOPSO and TRIS can be used.

The particles which can be the paramagnetic particles of U.S. Pat. No. 4,554,088 above, preferably have sizes in the range of 0.1 to 10$\mu$diameter. The particles are commercially used in amounts of 50 micrograms to 250 micrograms of solution and more preferably 60 to 75 micrograms of solution.

The carrier for the particles is preferably water which can be distilled, deionized or regular tap water, having minimal amounts of salts and the like which do not react adversely with the components of the aqueous suspensions of this invention.

The bulking agent chemical solutions of this invention are thiol blocked, if thiol groups are present and chemically reactive. Preferably, thiol blocked albumin is used since it is readily available and has good bulking properties. The thiol blocked proteins are preferably used in amounts of .05 to 4.0% by weight of the solution and more preferably .05 to 2.0%.

The suspensions can further have incorporated therein standard diagnostic reagents and the like including inorganic and organic salts and surfactants found in typical buffers and reagents.

Useful salts include sodium chloride, sodium citrate, magnesium and the chloride like benefactors include sodium dodocyl sulfate, tween and detergents.

According to the invention, the suspensions of this invention can be made by conventional mixing at room temperature. For example, water, buffering reagents and thiol blocked protein are admixed at room temperature with gentle stirring by rod to form stable suspensions and then the pH is adjusted as necessary. The solution is then filtered after which the particles are added to the solution.

The thiol group of the protein can be treated to block it by known reactions. Thiol blocked albumin having less than 0.02 moles sulfhydryl per mole of albumin is available commercially from Miles Laboratories (now Bayer), Kankakee, IL, USA (Miles Catalog No. 81-024™).

The suspensions of the present invention can be used in conventional diagnostic and detecting procedures. For example, the presence or absence of an analyte in a sample can be determined by combining the sample with particles for reaction with the analyte, a thiol blocked protein and water to form a suspension. The suspension is then placed under normal reaction conditions for the reaction to take place if the analyte is present. The suspension is monitored for the reaction product as an indication of the presence of an analyte.

The following examples are intended to illustrate and not to limit the invention.

EXAMPLE 1

This Example describes the relationship of a reactive thiol group in albumin with the formation of polymers. Four samples of BSA were prepared from a stock solution of 1% BSA, (Catalog No. 81-003™) (non thiol blocked) obtained from Miles Laboratories (now Bayer), Elkhardt, IN, USA, in 100 mM phosphate buffer pH 7.4. A first sample comprised a 1% BSA solution maintained at 4° C. for 16 hours. This sample was a control for monomer and thiol content. A value of 100% was assigned to Sample 1 with respect to these parameters as set forth in FIG. 2.

A second sample comprised a 1% solution of BSA maintained at neutral pH and heated 20 to 50° C. for 16 hours. A third sample was a 1% solution of BSA at neutral pH heated to 55° C. for 16 hours. A fourth sample comprised a 1% solution of BSA at neutral pH heated to 60° C. for 16hours.

After 16 hours size exclusion chromotographs were performed on the four samples. These data are presented in FIG. 3a with respect to Sample 1, FIG. 3b with respect to Sample 2, FIG. 3c with respect to Sample 3, and FIG. 3d with respect to Sample 4. These data are presented in bar graph form in FIG. 2.

Figure 2:
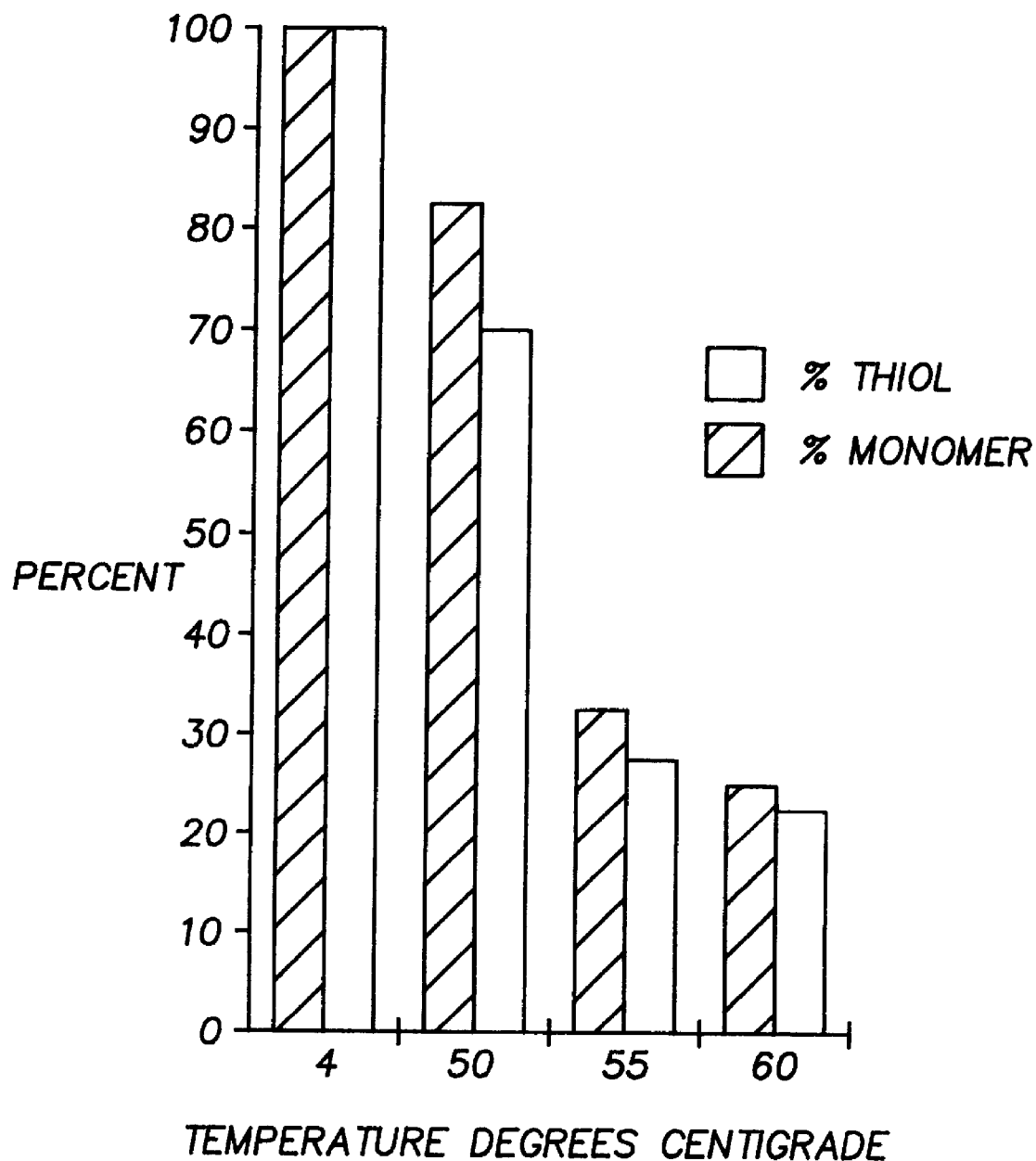
FIG. 2 is a graphical representation of the effect of temperature on BSA monomer content and thiol content.
Figure 3A:
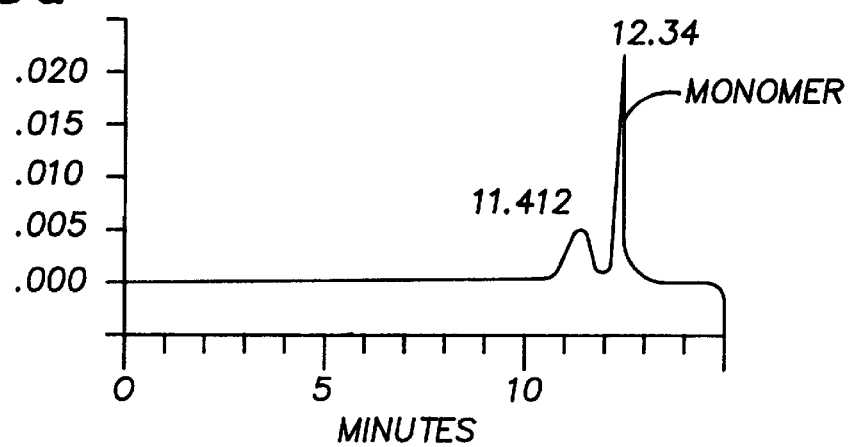
FIGS. 3a, 3b, 3c and 3d depict size exclusion chromatograms of bovine serum albumin at 4° C. after 16 hours, at 50° C. at 16 hours, at 55° C. at 16 hours and at 60° C. at 16 hours.
Figure 3B:
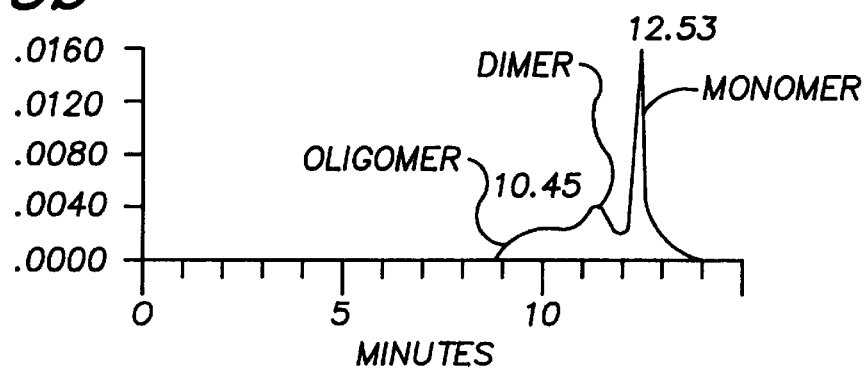
Figure 3C:
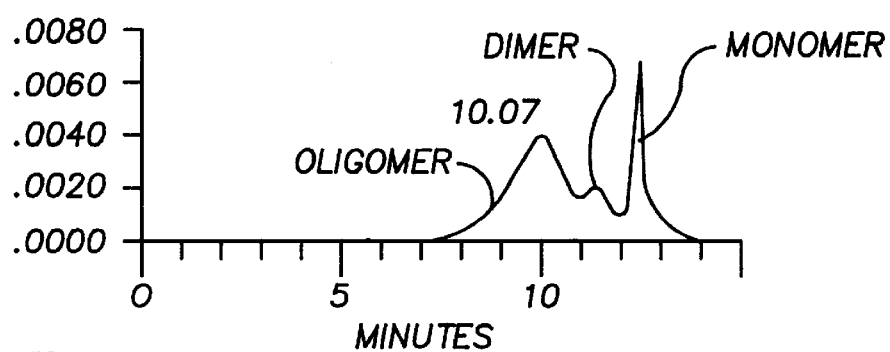
Figure 3D:
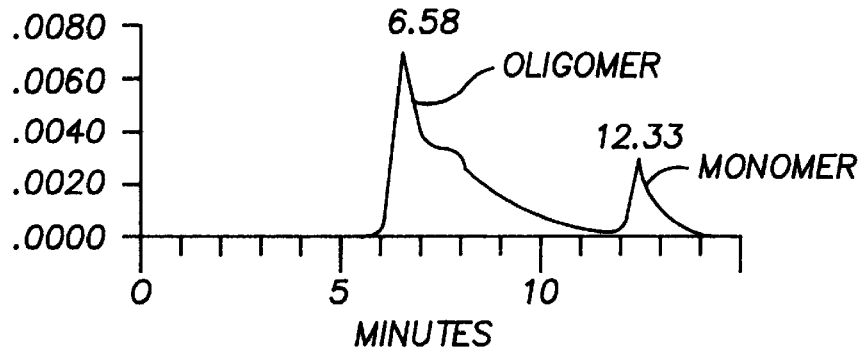

In FIG. 2, Sample 1 is a control value of 100% with respect to monomer concentration and thiol context. FIG. 1 depicts the percent monomer and thiol content versus the temperature in degrees Centigrade. Bars with angled lines depict monomer concentration. Bars without angled lines depict thiol concentration.

Compared to control Sample 1, Sample 2 heated to 50° C. exhibited a 17% reduction in monomer concentration and a 29% reduction in percent of thiol present.

Compared to the control Sample 1, Sample 3 heated to 55° C. exhibited 67% reduction in monomer concentration and a 74% reduction in percent active thiol.

Compared to control Sample 1, Sample 4 heated to 60° C. exhibited a monomer reduction of 76% and a reduction in reactive thiol of 78%.

The reduction in thiol concentration content of the BSA paralleled the reduction in monomer. Thus, the formation of BSA dimers and polymers was shown to be attributed, in part, to the thiol content of the monomer.

EXAMPLE 2

This example describes the relationship of thiol blocked albumin with the formation of fibrils and protein aggregates. Four samples of thiol-blocked BSA were prepared from a stock solution of 1% thiol-blocked BSA in 100 mM phosphate buffer. The thiol blocked BSA used in this Example is represented by the formula:

wherein P is albumin and X is represented by the formula:

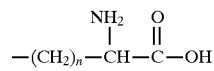

and n is 1. This thiol blocked BSA composition is formed by reacting the thiol group of the cysteine associated with albumin with a second cysteine to form a disulfide bond. This composition is available from Miles, Catalog No. 81-024™ as noted above The first sample, Sample 1, comprised a 1% thiol blocked BSA solution, which solution was maintained at 4° C. for 16 hours. This first sample was a control for monomer and reactive thiol content.

A second sample, Sample 2, comprised a 1% solution of thiol blocked BSA, which solution was maintained at neutral pH and heated to 50° C. for 16 hours. A third sample, Sample 3, comprised a 1% solution of thiol blocked BSA, which solution was maintained at neutral pH and heated to 55° C. for 16hours. A fourth sample, Sample 4, comprised a 1% solution of third blocked BSA which solution was maintained at neutral pH and heated to 60° C. for 16 hours.

Figure 4A:
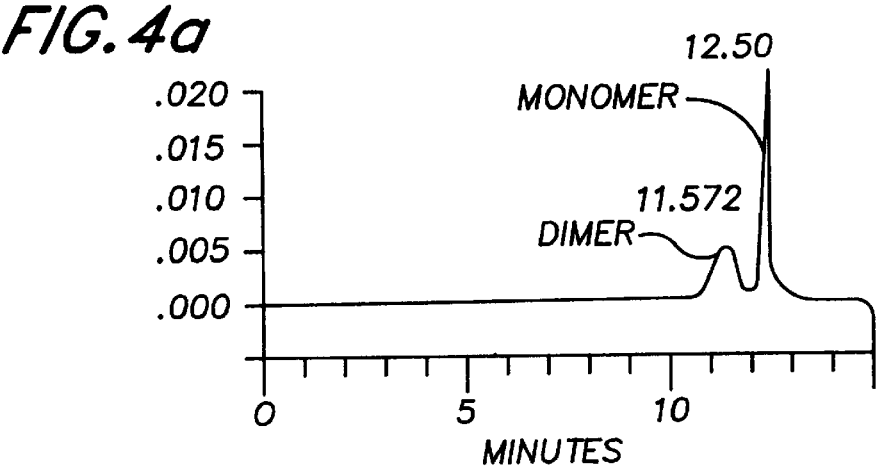
FIGS. 4a, 4b, 4c and 4d depict size exclusion chromatograms of thiol blocked bovine serum albumin at 4° C. after 16 hours, at 50° C. after 16 hours, at 55° C. after 16 hours and at 60° C. after 16 hours.
Figure 4B:
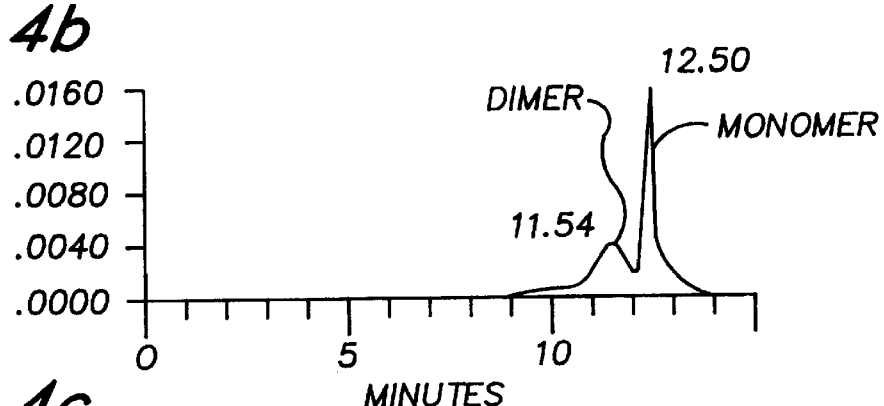
Figure 4C:
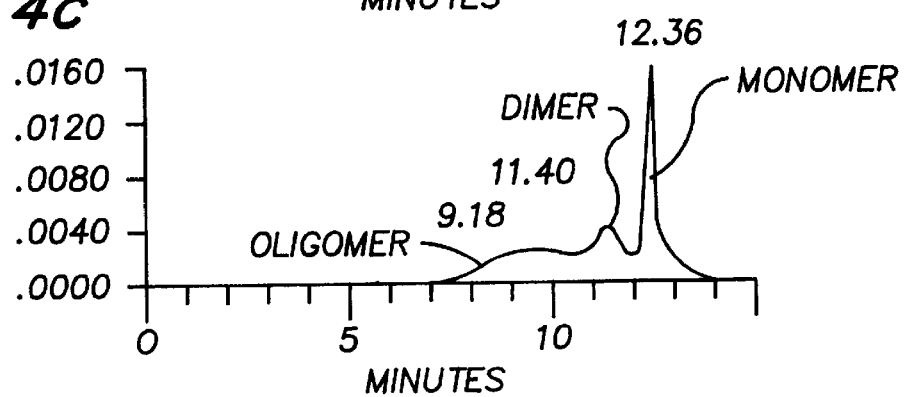
Figure 4D:
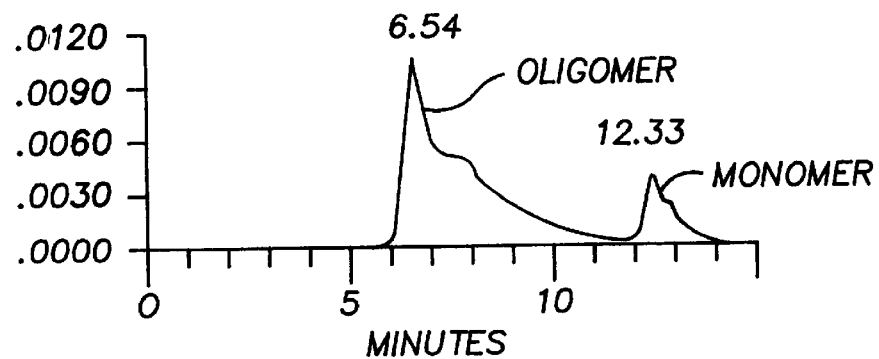

After 16 hours, size exclusion chromatographs were performed on each sample. These data are presented in FIG. 4a with respect to Sample 1; FIG. 4b with respect to Sample 2, FIG. 4c with respect to Sample 3, and, FIG. 4d with respect to Sample 4.

These data, compared to the data of Example 1, provide that the use of thiol-blocked BSA retarded clumping and fibril and aggregate formation. Samples 1–4 of Example 2 exhibited significantly less dimer formation and maintained a greater concentration of monomer than samples 1–4 of Example 1.

EXAMPLE 3

This example describes further comparisons of protein solutions with unblocked thiol groups with protein solutions in which the thiol group has been blocked. In this example, two stock solutions were made. A first stock solution comprised 5 mM barbital buffer at pH 8.5, 150 mM NaCl, 0.05% BSA and 0.15% bovine gamma globulin (BGG). The BSA and BGG contained unblocked thiol groups. That is, each had reactive thiol groups.

A second stock solution comprised 5 mM barbital buffer at pH 8.5, 150 mM NaCl, 0.05% thiol blocked BSA and 0.15% BGG. The thiol blocked BSA was as described in Example 2.

Five aliquots of the first stock solution were placed in five tissue culture flasks. Similarly, five aliquots of the second stock solution were placed in five tissue culture flasks. The resultant 10 samples, five containing unblocked thiol group BSA and five containing thiol blocked BSA were subjected to rocking motion at room temperature.

Samples containing unblocked thiol group BSA developed a sheet or membrane within thirty minutes. Samples containing thiol blocked BSA did not exhibit a sheet or membrane formation for approximately three hours. After twenty hours, the amount of clumping and aggregate formation exhibited in samples containing unblocked thiol group BSA exceeded the aggregate formation of the thiol blocked BSA.

EXAMPLE 4

This Example describes further the stability of thiol blocked BSA. In this Example, the protocol of Example 3 was repeated; however, the samples were subjected to rocking motion while being maintained at a temperature of 4° C.

Samples holding the thiol blocked BSA were free of visible aggregates for approximately 20 hours. However, samples containing unblocked thiol BSA exhibited aggregate formation.

EXAMPLE 5

This example features the preparation of a thiol blocked protein of the formula:

$$P—X$$

wherein P is albumin and X is an amine derivative of a $C_1$–$C_4$ alkoxy. More specifically, X is:

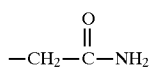

A one gram aliquot of albumin was dissolved in water. The pH of the solution was adjusted to pH 8.0 with sodium hydroxide solution. A molar excess, 3.3 mg. of iodoacetamide was added to the solution and stirred until the reaction was completed, approximately 2 hours. The thiol group of the cysteine amino acid of the albumin reacts with the iodoacetamide to form a thiol blocked albumin.

EXAMPLE 6

This example features a comparison of thiol blocked and unblocked BSA buffers and motion at different temperatures. Two aqueous stock solutions of bulking agent were made. The composition of this buffer is set forth below:

50 mM Sodium Barbital, 150 mM Sodium Chloride, 1 mM EDTA Tetra Sodium Salt, 0.5% w/v Sodium Azide, 0.05% w/v Bovine Serum Albumin (BSA), and 0.15 w/v Bovine Gamma Globulin (BGG) with final of pH 8.5.

One stock solution comprised normal BSA (non thiol blocked) and was prepared from Miles Lot 482. A second stock solution comprised blocked BSA sample and was prepared from Miles Lot 1017. Paramagnetic particles coupled with anti-prolactin mouse monoclonal were suspended in each stock solution. Aliquots of each stock solution were placed in tissue culture flasks. Each sample was rocked at room temperature. Each sample was inspected at various times and an assessment was made as to the degree of fibril or aggregate formation.

In the tables provided below, the following notations were used. Greater clumping is characterized by more "+"signs.

A "--" indicates no clumps were observed.

A "+"sign indicates a few clumps were observed.

A "+++++"sign indicates a large number of clumps were observed.

Table 1 sets forth the results where BSA Miles Lot 482 and BSA Miles Lot 1017 at pH 8.5 were rocked at room temperature.

TABLE 1

Degree of clumping (pH 8.5, Room temperature)

| Time Hours | BSA Lot 482 | BSA Lot 1017 |
|---|---|---|
| 1 | ++ | -- |
| 2 | ++ | -- |
| 3.5 | +++ | + |
| 8 | +++ | ++ |
| 18 | ++++ | ++ |

The data of Table 1 provide that thiol blocked BSA, BSA Miles Lot 1017, at pH 8.5 and subjected to rocking at room temperature provided more stable reagent suspension Table 2 sets forth the results where BSA Miles Lot 482 and BSA Miles Lot 1017 at pH 8.5 and held at 4° C. and subjected to rocking.

TABLE 2

Degree of Clumping (pH 8.5, 4° C.)

| Time Hours | BSA Lot 482 | BSA Lot 1017 |
|---|---|---|
| 1 | -- | -- |
| 2 | -- | -- |
| 3 | -- | -- |
| 4 | + | -- |
| 20 | +++ | -- |

The data of Table 2 provide that thiol blocked BSA, BSA Miles Lot 1017 at pH 8.5 and at 4° C. and subjected to rocking provided more stable reagent suspensions.

Two aqueous stock solutions were made of 0.1 M phosphate buffer pH 7.5 with 1% BSA. One stock solution was made with unblocked BSA and designated BSA Miles Lot 482. One was made with thiol blocked BSA and was designated BSA Miles Lot 1017. These two stock solutions also received anti-prolactin mouse monoclonal antibody bonded paramagnetic particles.

Table 3 sets forth the results of BSA Miles Lot 482 and BSA Miles Lot 1017, at pH 7.5 held at room temperature and subjected to rocking.

TABLE 3

Degree of clumping (pH 7.5, Room temperature)

| Time Hours | BSA Lot 482 | BSA Lot 1017 |
|---|---|---|
| 2 | -- | -- |
| 4 | -- | -- |
| 6 | -- | -- |
| 23 | ++++ | -- |
| 29 | ++++ | -- |

The data of Table 3 provide that the thiol blocked BSA, BSA Miles Lot 1017, at pH 7.5 and at room temperature and subjected to rocking, produced more stable reagent suspensions.

Thus, while preferred embodiments of the invention have been described, the present invention is capable of variation and modification and, therefore, the present invention should not be limited to the precise details set forth, but should include such changes and alterations as fall within the purview of the following claims.

I claim:

1. A reagent suspension comprising, an aqueous suspending agent, a plurality of particles for coupling with a reactant capable of reacting with an analyte and a thiol blocked protein carried by said suspension and having the formula:

P—X wherein P is a protein having one or more thiol groups and X is a blocking group covalently bonded to said thiol group, such that the thiol group is blocked or chemically inert wherein siad thiol blocked protein is present in an amount sufficient to reduce aggregation or fibril formation.

2. The suspension of claim 1, wherein said blocking groups comprise: $C_1$–$C_{12}$ alkyl, $C_3$–$C_{12}$ cycloalkyl, $C_1$–$C_{12}$ haloalkyl, $C_1$–$C_{12}$ hydroxyalkyl, $C_2$–$C_{12}$ alkenyl, $C_2$–$C_{12}$ haloalkenyl, $C_1$–$C_{12}$ hydroxyalkenyl, $C_2$–$C_{12}$ alkynyl, $C_3$–$C_{12}$ haloalkynyl, $C_2$–$C_6$ hydroxyalkynyl, $C_6H_5$, $C_1$–$C_{10}$alkoxy, $C_1$–$C_{10}$ haloalkoxy, $C_1$–$C_{10}$ hydroxyalkoxy, $C_1$–$C_{10}$ alkylthio, $C_1$–$C_{10}$ alkylsulfinyl, $C_1$–$C_{10}$alkylsulfonyl, and amine, amide and imide substitutions and derivatives thereof.

3. The suspension of claim 1, wherein P is albumin and said suspending agent is water.

4. The suspension of claim 3, wherein said albumin is derived from one of the following sources consisting of human, bovine, porcine and poultry sources.

5. The suspension of claim 1, wherein X consists of:

—S—R wherein R is $C_1$–$C_{12}$ alkyl, $C_3$–$C_{12}$ cycloalkyl, $C_1$–$C_{12}$ haloalkyl, $C_1$–$C_6$ hydroxyalkyl, $C_2$–$C_{12}$ alkenyl, $C_2$–$C_{12}$ haloalkenyl, $C_2$–$C_{12}$ hydroxyalkenyl, $C_2$–$C_{12}$ alkynyl, $C_2$–$C_{12}$ haloalkynyl, $C_2$–$C_{12}$hydroxyalkynyl, $C_6H_5$, $C_1$–$C_{10}$ alkoxy, $C_1$–$C_{10}$ haloalkoxy, $C_1$–$C_{10}$ hydroxyalkoxy, $C_1$–$C_4$ alkylthio, $C_1$–$C_4$ alkylsulfinyl, $C_1$–$C_4$ alkylsulfonyl, and amine, amide, and imide substitutions and derivatives thereof.

6. The suspension of claim 5, wherein R is:

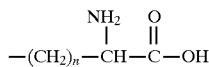

wherein n is an integer from 1 to 3.

7. The suspension of claim 6, wherein n is 1.

8. The suspension of claim 1, wherein X is:

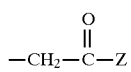

wherein Z is hydroxyl, $C_1$–$C_6$ alkyl, $C_3$–$C_6$ cycloalkyl, $C_1$–$C_6$ haloalkyl, $C_1$–$C_6$ hydroxyalkyl, $C_2$–$C_6$ alkenyl, $C_2$–$C_6$ haloalkenyl, $C_2$–$C_6$ hydroxyalkenyl, $C_2$–$C_6$ alkynyl, $C_2$–$C_6$ haloalkynyl, $C_2$–$C_6$ hydroxyalkynyl, $C_6H_5$, $C_1$–$C_4$ alkoxy, $C_1$–$C_4$ haloalkoxy, $C_1$–$C_4$ hydroxyalkoxy, $C_1$–$C_4$ alkylthio, $C_1$–$C_4$ alkylsulfinyl, $C_1$–$C_4$ alkylsulfonyl, and amine, amide, imide and thiol substitutions and derivatives thereof, or Z is

wherein U or W independently are hydrogen, $C_1$–$C_6$ alkyl, $C_3$–$C_6$ cycloalkyl, $C_1$–$C_6$ haloalkyl, $C_1$–$C_6$ hydroxyalkyl, $C_2$–$C_6$ alkenyl, $C_2$–$C_6$ haloalkenyl, $C_2$–$C_6$ hydroxyalkenyl, $C_2$–$C_6$ alkynyl, $C_3$–$C_6$ haloalkynyl, $C_3$–$C_6$ hydroxyalkynyl, $C_6H_5$, $C_1$–$C_4$ alkoxy, $C_1$–$C_4$ haloalkoxy, $C_1$–$C_4$ hydroxyalkoxy, $C_1$–$C_4$ alkylthio, $C_1$–$C_4$ alkylsulfinyl, $C_1$–$C_4$ alkylsulfonyl, and amine, amide, and imide substitutions and derivatives thereof.

9. The suspension of claim 3, wherein said particles are paramagnetic and have a diameter of from 0.1 to 10 $\mu$.

10. The suspension of claim 1, wherein said particles are paramagnetic and said suspension is carried by a plastic container.

11. A method of making a reagent suspension comprising the steps of combining water and a thiol blocked protein, and one or more solid phase materials wherein said thiol blocked. protein is present in an amount sufficient to reduce aggregation of fibril formation.

12. A method of detecting the presence or absence of an analyte in an aqueous sample positioned in a plastic container, said method comprising, combining said sample with paramagnetic particles carrying a reactant for reaction with said analyte, a thiol blocked protein, present in an amount aggregation or fibril formation and water to form a suspension of said particles and thiol blocked protein which suspension resists aggregate formation of said thiol blocked protein;

imposing reaction conditions on said suspension to form a reaction product in the presence of analyte; and, monitoring the suspension for said reaction product as an indication of the presence of said analyte.

13. The method of claim 12, wherein said thiol blocked protein is comprised of the formula:

P—X wherein P is a protein having a thiol group and X is a blocking group covalently bonded to said thiol group, said blocking group consisting of $C_1$–$C_{12}$ alkyl, $C_3$–$C_{12}$ cycloalkyl, $C_1$–$C_{12}$ haloalkyl, $C_1$–$C_{12}$ hydroxyalkyl, $C_2$–$C_6$ alkenyl, $C_2$–$C_6$ haloalkenyl, $C_2$–$C_{12}$ hydroxyalkenyl, $C_2$–$C_{12}$ alkynyl, $C_3$–$C_1$ haloalkynyl, $C_2$–$C_2$ hydroxyalkynyl, $C_6H_5$, $C_1$–$C_4$ alkoxy, $C_1$–$C_{10}$ haloalkoxy, $C_1$–$C_1$hydroxyalkoxy, $C_1$–$C_{10}$ alkylthio, $C_1$–$C_1$ alkylsulfinyl, $C_1$–$C_{10}$ alkylsulfonyl, and amine, amide, and imide substitutions and derivatives thereof.

14. The method of claim 12, wherein X consists of:

—S—R wherein R is $C_1$–$C_6$ alkyl, $C_3$–$C_6$ cycloalkyl, $C_1$–$C_6$ haloalkyl, $C_1$–$C_{10}$ hydroxyalkyl, $C_2$–$C_6$ alkenyl, $C_2$–$C_6$ haloalkenyl, $C_2$–$C_6$ hydroxyalkenyl, $C_2$–$C_6$ alkynyl, $C_2$–$C_6$ haloalkynyl, $C_2$–$C_6$ hydroxyalkynyl, $C_6H_5$, $C_1$–$C_4$ alkoxy, $C_1$–$C_4$ haloalkoxy, $C_1$–$C_4$ hydroxyalkoxy, $C_1$–$C_4$ alkylthio, $C_1$–$C_4$ alkylsulfinyl, $C_1$–$C_4$ alkylsulfonyl, and amine, amide, and imide substitutions and derivatives thereof.

15. The method of claim 12 wherein said protein is a thiol blocked albumin and said particles are paramagnetic particles having a diameter of from about 0.1 to 10$\mu$in diameter.

* * * * *